United States Patent [19]

Gross

[11] Patent Number: 5,961,504

[45] Date of Patent: *Oct. 5, 1999

[54] METHOD FOR REDUCING MALODOR IN ABSORBENT PRODUCTS AND PRODUCTS FORMED THEREBY

[75] Inventor: James Richard Gross, Appleton, Wis.

[73] Assignee: Kimberly-Clark Worldwide, Inc., Neenah, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/164,112

[22] Filed: Dec. 7, 1993

Related U.S. Application Data

[63] Continuation-in-part of application No. 07/858,477, Mar. 27, 1992, abandoned.

[51] Int. Cl.⁶ .................................................... A61F 13/15
[52] U.S. Cl. .......................................... 604/358; 604/360
[58] Field of Search ................................. 604/359, 360, 604/369

[56] References Cited

U.S. PATENT DOCUMENTS

| | | |
|---|---|---|
| 2,298,424 | 10/1942 | Schreiber . |
| 3,805,790 | 4/1974 | Kaczmarzyk et al. . |
| 3,881,490 | 5/1975 | Whitehead et al. . |
| 3,903,259 | 9/1975 | Hart . |
| 4,017,653 | 4/1977 | Gross . |
| 4,093,776 | 6/1978 | Aoki et al. . |
| 4,182,827 | 1/1980 | Jones et al. . |

(List continued on next page.)

FOREIGN PATENT DOCUMENTS

| | | |
|---|---|---|
| B-51448/79 | 6/1980 | Australia . |
| A-14879/92 | 10/1992 | Australia . |
| 0009977A1 | 4/1980 | European Pat. Off. . |
| 0063331A3 | 10/1982 | European Pat. Off. . |
| 0255701A2 | 2/1988 | European Pat. Off. . |
| 0395099A2 | 10/1990 | European Pat. Off. . |
| 0434523A1 | 6/1991 | European Pat. Off. . |
| 0509708A1 | 10/1992 | European Pat. Off. . |
| 1307930 | 9/1962 | France . |
| 61-2717 | 1/1986 | Japan . |
| 61-217168 | 9/1986 | Japan . |
| WO 95/24173 | 9/1995 | WIPO . |

OTHER PUBLICATIONS

Surface Active Agents and Detergents—vol. II—1958—by Anthony M. Schwartz, James W. Perry, Julian Berch—Interscience Publishers, Inc., New York, pp. 479–480.

Chemistry of Organic Compounds—3rd Edition—1965—by Carl R. Noller—W. B. Saunders Company, Philadelphia and London, p. 867.

Database WPIL. Week 8642, Derwent Publications Ltd., London, GB; AN 86–275168 & JP–A–61 200 102 (Showa Denko KK) (Abstract).

Database WPIL. Week 8644, Derwent Publications Ltd., London, GB; AN 86–287743 & JP–A–61 209 658 (Shiseido KK) (Abstract).

*Primary Examiner*—John G. Weiss
*Assistant Examiner*—Dennis Ruhl
*Attorney, Agent, or Firm*—Thomas J. Connelly; Sebastian C. Pugliese, III; Douglas G. Glantz

[57] ABSTRACT

Disclosed is a method for reducing the malodor associated with disposable absorbent products intended for the absorption of body fluids. The method involves applying to the absorbent product, prior to its use, an effective amount of a surface-active agent having a hydrophilic/lipophilic balance of less than about 12. The surface-active agent is effective to reduce the odor of urine. Also disclosed is a disposable absorbent product intended for the absorption of body fluids, which disposable absorbent product includes an absorbent structure including a water-swellable, generally water-insoluble, hydrogel-forming polymeric absorbent material, a covering material, and an effective amount of a surface-active agent having a hydrophilic/lipophilic balance of less than about 12. The surface-active agent is effective to reduce the odor of urine.

11 Claims, 1 Drawing Sheet

U.S. PATENT DOCUMENTS

| | | |
|---|---|---|
| 4,190,563 | 2/1980 | Bosley et al. . |
| 4,263,363 | 4/1981 | Buck et al. .............................. 604/369 |
| 4,315,507 | 2/1982 | Whitehead et al. . |
| 4,340,706 | 7/1982 | Obayashi et al. . |
| 4,381,782 | 5/1983 | Mazurak et al. ........................ 604/369 |
| 4,426,210 | 1/1984 | Drawert et al. . |
| 4,435,172 | 3/1984 | Gross . |
| 4,438,009 | 3/1984 | Brusky et al. . |
| 4,459,396 | 7/1984 | Yamaski et al. . |
| 4,606,958 | 8/1986 | Haq et al. . |
| 4,611,014 | 9/1986 | Jomes et al. . |
| 4,647,636 | 3/1987 | Makita et al. . |
| 4,655,877 | 4/1987 | Horimoto et al. . |
| 4,698,404 | 10/1987 | Cramm et al. . |
| 4,710,187 | 12/1987 | Boland et al. . |
| 4,721,647 | 1/1988 | Nakanishi et al. . |
| 4,732,968 | 3/1988 | Obayashi et al. . |
| 4,742,086 | 5/1988 | Masamizu et al. . |
| 4,755,562 | 7/1988 | Alexander et al. . |
| 4,762,521 | 8/1988 | Roessler et al. . |
| 4,770,656 | 9/1988 | Proxmire et al. . |
| 4,777,232 | 10/1988 | Heidel . |
| 4,789,588 | 12/1988 | Suzuki et al. . |
| 4,798,603 | 1/1989 | Meyer et al. . |
| 4,816,220 | 3/1989 | Roychowdhury . |
| 4,977,208 | 12/1990 | Hosoya et al. . |
| 5,149,750 | 9/1992 | Niessner et al. . |
| 5,180,800 | 1/1993 | Heidel et al. . |
| 5,214,075 | 5/1993 | Engelhardt et al. . |

METHOD FOR REDUCING MALODOR IN ABSORBENT PRODUCTS AND PRODUCTS FORMED THEREBY

The present application is a continuation-in-part of Ser. No. 07/858,477, filed Mar. 27, 1992, now abandoned.

BACKGROUND OF THE INVENTION

1. Field of the Invention

The present invention relates to a method for reducing the malodor associated with disposable absorbent products intended for the absorption of body fluids and a product formed by the method.

2. Description of the Related Art

Absorbent products intended to absorb discharged body fluids are well known in the art. Such absorbent products generally comprise a fibrous mass capable of absorbing and holding such body fluids. Similarly, it is well known that, after use, absorbent products intended to absorb urine, for example, may have an unpleasant odor. In order to render the use and changing of absorbent products less objectionable, a variety of solutions have been proposed to deal with reducing or masking malodors associated with used absorbent products.

For example, U.S. Pat. No. 3,903,259 issued Sep. 2, 1975, to Hart describes a method of deodorizing diapers and human excreta. The method comprises applying to the used diapers a chemical composition which, in its simplest form, consists of an acidic material, an antibacterial material and a solvent.

Alternatively, many disposable absorbent products contain perfuming agents which are intended to mask malodors associated with the used product. The use of masking agents, such as perfumes, is not entirely successful, as some individuals exhibit skin or respiratory sensitivities to such perfuming agents. Further, as the perfuming agent does not eliminate the malodors associated with the used absorbent products, the odor which results from the combination of the used absorbent product and perfuming agent is not always pleasant.

Absorbent products such as disposable diapers, adult incontinence products, training pants, and feminine care products often employ water-swellable, generally water-insoluble absorbent materials known in the art as superabsorbents. Such superabsorbents are generally capable of absorbing at least about 10, and up to 100 times their weight in water. The use of such superabsorbent materials in absorbent products greatly increases the absorbent capacity of the absorbent products while allowing for a reduction in their bulk. In recent years, the concentration of superabsorbent materials used in absorbent products has been increasing. Specifically, when superabsorbents were first introduced into absorbent products, the superabsorbents generally comprised only a small portion of the absorbent structure present in the absorbent products. Currently, it is not unusual for the superabsorbents to comprise 30 weight percent, 50 weight percent, or even more of the absorbent structure in the absorbent products. As the concentration of superabsorbents increases, the overall bulk of the absorbent product decreases. This is desirable in that it allows for smaller, less bulky absorbent products.

Unfortunately, as the concentration of superabsorbent materials used in disposable products increases, so do the malodors associated with such products. Specifically, Applicant believes that the superabsorbent materials have a greater affinity for the water present in the body fluid than for the dissolved odiferous compounds. Thus, the presence of the superabsorbent materials is believed to concentrate the odor causing compounds resulting in an intensification of the natural odors. In some instances, desolvation of the odiferous compounds may occur.

It is desirable to find an efficient and effective manner to reduce the malodors associated with absorbent products containing relatively high concentrations of superabsorbent material without relying completely on masking agents such as perfumes.

SUMMARY OF THE INVENTION

The present invention concerns a method for reducing malodor associated with disposable absorbent products intended for the absorption of body fluids. The method comprises the steps of applying to an absorbent product, including a water-swellable, generally water-insoluble, hydrogel-forming polymeric absorbent material, prior to its use, an effective amount of a surface-active agent having a hydrophilic/lipophilic balance (HLB) of less than about 12. The surface-active agent is effective to reduce the odor of urine.

In another aspect, the present invention concerns a disposable absorbent product for the absorption of body fluids. The absorbent product comprises an absorbent structure comprising from about 10 to 100 weight percent, based on absorbent structure weight, of a water-swellable, generally water-insoluble, hydrogel-forming polymeric absorbent material. At least 2 percent of the absorbent material has a particle size of less than about 200 micrometers. A covering material at least partially covers an outer surface of the absorbent structure. The absorbent product further comprises an effective amount of a surface-active agent having a hydrophilic/lipophilic balance (HLB) of less than about 12, the surface-active agent being effective to reduce the odor of urine.

DETAILED DESCRIPTION OF THE PREFERRED EMBODIMENTS

In one aspect, the present invention relates to a method for reducing malodor associated with disposable absorbent products intended for the absorption of body fluids. Such absorbent products are known and include diapers, training pants, adult incontinence products, feminine napkins, tampons, and the like. For ease of understanding, the present invention will be explained in terms of an infant diaper, such as that illustrated in FIG. 1, and a feminine napkin, such as that illustrated in FIG. 2. Nonetheless, it is understood that the invention is equally applicable to other absorbent products intended to absorb body fluids.

Such absorbent products generally comprise an absorbent structure and a covering layer which covers at least a portion of an outer surface of the absorbent structure. In the case of diapers, the covering layer often comprises two pieces consisting of a liquid-permeable bodyside liner adapted to contact the skin of a wearer and a liquid-impervious outer cover. The absorbent structure is located between the bodyside liner and the outer cover which may be joined along their periphery. The absorbent structure generally comprises an amount of a water-swellable, generally water-insoluble, hydrogel-forming polymeric absorbent material known in the art as a superabsorbent. The absorbent structure generally comprises a superabsorbent in an amount of from about 10 to 100 weight percent, from about 30 to 100 weight percent, from about 50 to 100 weight percent, or from about 60 to 100 weight percent, based on total weight of the absorbent structure. The absorbent structure generally further comprises a means, such as a fibrous material, e.g., wood pulp fluff, synthetic polymeric fibers, or the like, for containing the superabsorbent material. Such fibers may form a matrix in which the superabsorbent material can be contained. Suitably, the means of containing the superabsorbent material comprises a hydrophilic substrate. Other means of containing the superabsorbent material, such as foams, laminates, and the like, are known and suited for use in the present invention. When the absorbent structure comprises about 100 weight percent superabsorbent, the superabsorbent may, for example, be contained in place between two flexible fiber sheets such as a tissue wrap sheet or spunbond material. Suitably, the absorbent products or absorbent structures of the present invention do not include an oleophilic substrate, such as a porous oleophilic substrate having a void volume of at least 50 percent of the total volume of the porous oleophilic substrate.

Superabsorbent materials suitable for use in the present invention are known to those skilled in the art. As a general rule, the water-swellable, generally water-insoluble, hydrogel-forming polymeric absorbent material (superabsorbent) is capable of absorbing at least about 10, desirably about 20, and possibly about 100 times or more its weight in water. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors such as The Dow Chemical Company, Hoechst Celanese Corporation, Allied Colloid Inc., and Stockhausen, Inc.

Non-cellulosic synthetic hydrogel-forming polymers may be formed through a suspension (including inverse suspension) or solution polymerization process. In a suspension polymerization process, monomeric material from which the absorbent material is to be formed is suspended in an inert medium and subsequently polymerized. In a solution polymerization process, the monomers from which the absorbent material is to be formed are dissolved in an aqueous phase and subsequently polymerized, dried, and ground into particles having a desired particle size range.

In one preferred embodiment of the present invention, the non-cellulosic, synthetic hydrogel-forming polymers are preferred for use. Specifically, it is preferred that the absorbent material be selected from the group consisting of alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridines, hydrolyzed acrylonitrile grafted starch, acrylic acid grafted starch, and isobutylene maleic anhydride copolymers and mixtures thereof. It is further preferred that the synthetic hydrogel-forming polymers be formed through a solution polymerization process.

The absorbent material is typically in the form of discrete particles. Nonetheless, the absorbent material may be in a wide variety of other geometric forms such as fibers, flakes, spheres, and the like. When the absorbent material is in the form of discrete particles or spheres, the particles or spheres may generally have a maximum cross-sectional dimension of from about 10 micrometers to about 2,000 micrometers, or of from about 60 micrometers to about 1,000 micrometers. The particles or spheres, when present in the absorbent structures of the described absorbent products, may, but need not, generally have a relatively broad particle size distribution. For example, at least about 2 weight percent, or at least about 3 weight percent, of the absorbent material may have a particle size (maximum cross-sectional dimension) less than about 200 micrometers, while some of the absorbent material may have a maximum cross-sectional dimension of 800 micrometers or greater.

According to the method of the present invention, there is applied to an absorbent product, including a water-swellable, generally water-insoluble, hydrogel-forming polymeric absorbent material, prior to its use, an effective amount of a surface-active agent having a hydrophilic/lipophilic balance (HLB) of less than about 12, desirably less than about 11, suitably in a range of greater than 7 to about 12, more suitably in a range of greater than 7 to about 11. The surface-active agent is effective to reduce the odor of urine.

As used herein, the term "surface-active agent" refers to any compound or mixture of compounds that reduces surface tension when dissolved or dispersed in water or water solutions, or which reduces interfacial tension between two liquids, or between a liquid and a solid.

As used herein, the term "hydrophilic/lipophilic balance (HLB)" refers to the HLB numbering system developed at the Atlas Powder Company, and now used worldwide, to rank surface-active agents by relative water or oil solubility. In general, compounds represented by numbers below about 12 are oil soluble, those above about 12 are water soluble. A more complete description of the HLB system is found on page 479 et seq. of *Surface Active Agents and Detergents,* Volume II, (Interscience Publishers, Inc., 1958).

Surface-active agents having a hydrophilic/lipophilic balance of less than 12 are generally, non-ionic, but may be anionic, or cationic. As discussed above, surface-active agents with an HLB of less than about 12 are generally water insoluble and suited for use in preparing water-in-oil emulsions. A listing of surface-active agents having an HLB of less than 12 can be found in *McCutcheon's Emulsifiers and Detergents,* International or North American Edition.

Not all of the surface-active agents having an HLB of less than 12 are able to reduce the odor of urine. Applicant has devised a simple test to determine whether or not a given surface-active agent, having an HLB of less than 12, is capable of reducing the odor of urine. The test method for determining whether or not a surface-active agent is able to reduce the odor of urine (Surface-Active Agent Effectiveness Test) is set forth in connection with the examples which follow. If a surface-active agent has an HLB of less than 12 and is capable of reducing the odor of urine, it is believed suitable for use in the present invention. Obviously, it is desirable that the surface-active agents not deleteriously affect the product product in which it is to be incorporated.

It is anticipated that surface-active agents capable of reducing the odor of urine may be able to reduce the odor of other body fluids, such as menses. This is because the odor-causing compounds present in urine and menses are in some ways similar. Nonetheless, it is not necessary that the surface-active agent employed be capable of reducing the odor of menses.

Any method of applying the surface-active agent to the absorbent product is believed suitable for use in the present invention. The Applicant has incorporated the surface-active agent into the superabsorbent material during polymerization, has coated the superabsorbent material with the surface-active agent after polymerization, has coated inert particles with the surface-active agent and incorporated the inert particles in the absorbent hydrophilic-substrate structure, and has sprayed a solution containing the surface-active agent directly on the absorbent hydrophilic-substrate structure. As will be shown in the examples, all of the methods discussed above have proven suitable for use in the present method. Thus, the Applicant believes that any method of incorporating the surface-active agent in the absorbent product is suitable for use in the present invention. Suitably, the surface-active agent is not applied to the absorbent product, the hydrogel-forming polymeric absorbent material, or to an oleophilic substrate of the absorbent product, as an oily, self-emulsifying concentrate comprising an oil or hydrocarbon solvent. Suitably, if the surface-agent is added to the superabsorbent material during polymerization, none of the surface-active agent is added to the reaction mixture after the monomers have undergone not less than 60 percent conversion.

It is generally believed desirable to locate the surface-active agent in that area of the absorbent product which is most likely to be exposed to the body fluid intended to be absorbed. Thus, in the case of a diaper, the surface-active agent would generally be present in the from portion and crotch portion of the diaper.

Surface-active agents suitable for use in the present invention (as determined by the Surface-Active Agent Effectiveness Test set forth below) include an ethoxylated sorbitan mono-oleate (HLB 10), commercially available from ICI Americas, Inc. under the trade designation TWEEN™ 81; sorbitan mono-oleate (HLB 4.3), commercially available from ICI Americas, Inc. under the trade designation SPAN™ 80; and ethoxylated $C_{11}$–$C_{15}$ secondary alcohols (HLB 10.6), commercially available from Union Carbide Corporation under the trade designation TERGITOL™ 15-S-5.

The following surfactants have proven to be unsuitable for use in the present invention in that they are not able to reduce the odor of urine as determined by the Surface-Active Agent Effectiveness Test set forth in connection with the examples: glycerol monostearate (HLB 5.0), commercially available from Inolex Chemical Company under the trade designation LEXEMUL™ 530; ethoxylated nonyl phenols, commercially available from GAF Chemicals Corporation under the trade designation IGEPAL™ CO-210 (HLB 4.6) and CO-430 (HLB 8.8); and ethoxylated linear $C_{30}$ alcohols (HLB 10), commercially available from Petrolite Specialty Polymers Group under the trade designation UNITHOX™ 450.

The surface-active agents are applied to the absorbent products in an amount effective to reduce the odor of the absorbed body fluid. Applicant has found some evidence to suggest that the odor-reducing capabilities (at least with respect to urine) of the surface-active agents are, within certain limitations, dependent on the amount of the surface-active agent present in the absorbent products. Thus, relatively low levels (less than about 0.1 weight percent, based on total absorbent structure weight) of the surface-active agent may be effective to reduce the odor associated with an absorbed body fluid. At relatively high concentrations of surface-active agent (greater than about 5 weight percent based on total weight of the absorbent structure), the malodor associated with the absorbent product may be reduced to a much greater extent. Thus, the amount of surface-active agent desirably present in the absorbent product depends, to a degree, on the amount of odor reduction desired. Any amount of surface-active agent effective to perceptibly reduce the odor associated with the used absorbent product is suitable for use in the present invention. As a general rule, the surface-active agent will be present in the absorbent product in an amount of from about 0.005 to about 25 weight percent, based on total weight of the absorbent structure, of from about 0.1 to about 10 weight percent, based on total weight of the absorbent structure, or of from about 0.5 to about 5 weight percent, based on total weight of the absorbent structure.

As discussed above, the need for odor reduction may be most noticeable when the absorbent structures contain a relatively high concentration of a water-swellable, generally water-insoluble, hydrogel-forming polymeric absorbent material. Thus, when the absorbent structure contains greater than about 30 weight percent of such a water-swellable, generally water-insoluble, hydrogel-forming polymeric absorbent material, it is generally desired that the surface-active agent be present in the absorbent product in an amount of from about 0.005 to about 25 weight percent, of from about 0.1 to about 10 weight percent, or of from about 0.5 to about 5 weight percent based on total weight of the water-swellable, generally water-insoluble, hydrogel-forming polymeric absorbent material present in the absorbent product.

As a general rule, the surface-active agent will be present in the absorbent structure in an amount of less than about 20 weight percent, preferably of less than about 10 weight percent, or of less than about 5 weight percent, based on total weight of the water-swellable, generally water-insoluble, hydrogel-forming polymeric absorbent material present in the absorbent structure.

In a second aspect, the present invention concerns a disposable absorbent product intended for the absorption of body fluids. The absorbent body comprises an absorbent structure comprising from about 10 to 100 weight percent, based on absorbent structure weight, of a solution polymerized, water-swellable, generally water-insoluble, hydrogel-forming polymeric absorbent material wherein at least about 2 weight percent of said absorbent material has a particle size of less than about 200 micrometers; a covering material at least partially covering an outer surface of the absorbent structure; and an effective amount of a surface-active agent having a hydrophilic/lipophilic balance of less than about 12. The surface-active agent is effective to reduce the odor of urine.

Figure 1:
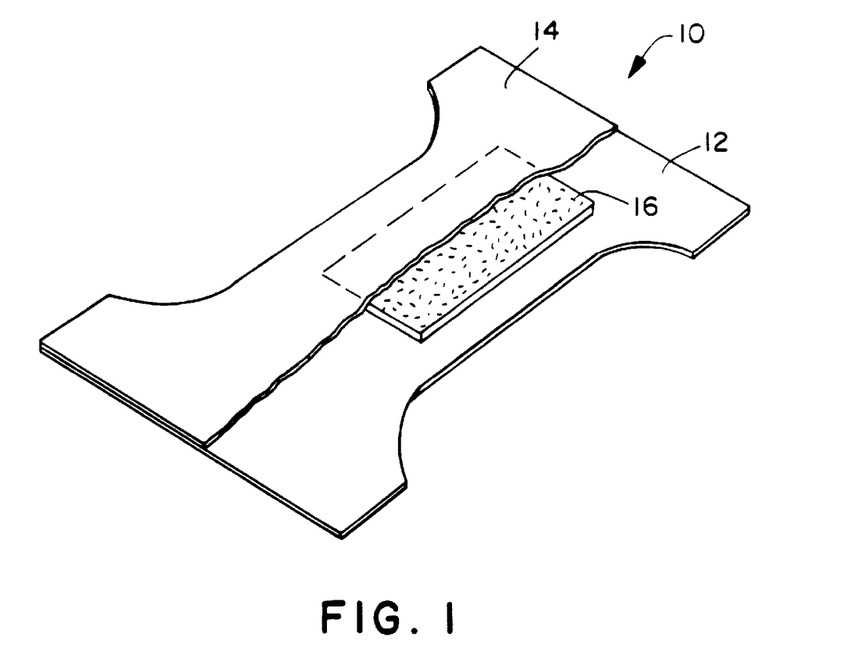
FIG. 1 represents a disposable diaper according to the present invention.

This aspect of the present invention can best be understood by reference to FIG. 1 wherein a disposable diaper 10 is illustrated. Disposable diaper 10 comprises an outer covering material consisting of backing sheet 12 and bodyside liner 14 and an absorbent structure 16 located between backing sheet 12 and bodyside liner 14. The absorbent structure suitably has the construction hereinbefore defined. In one preferred embodiment, the absorbent structure comprises a fibrous matrix comprising from about 10 to 100 weight percent, from about 30 to about 100 weight percent, from about 50 to 100 weight percent, or from about 60 to about 100 weight percent, based on total absorbent structure weight, of a water-swellable, generally water-insoluble, hydrogel-forming polymeric absorbent material. The fibrous matrix suitably comprises wood pulp fibers or synthetic polymeric fibers.

Figure 2:
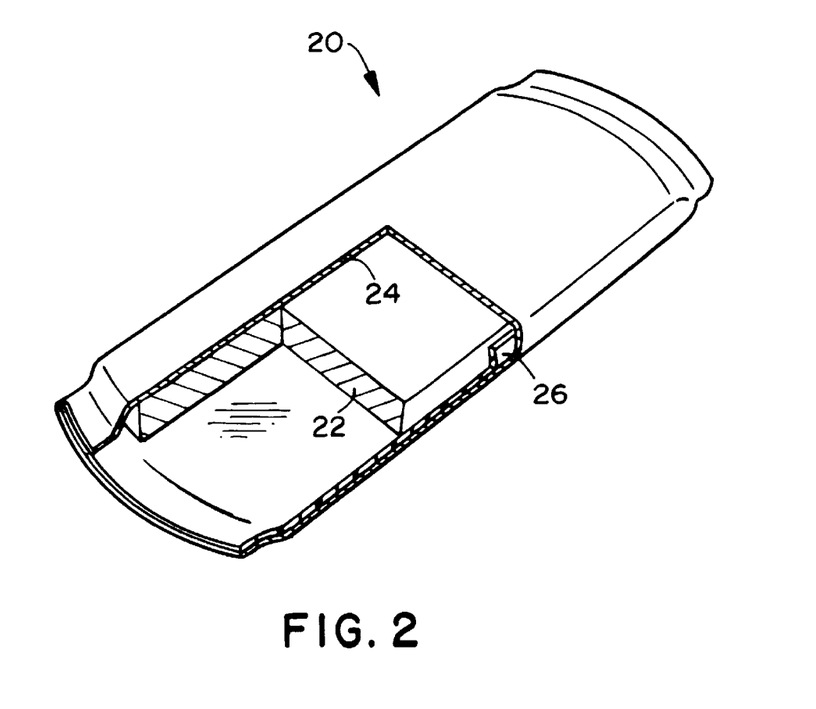
FIG. 2 illustrates a feminine napkin according to the present invention.

FIG. 2 illustrates a feminine napkin according to the present invention. The feminine napkin 20 comprises an absorbent structure 22, an outer covering 24, and a liquid-impervious baffle 26.

Absorbent products are described in U.S. Pat. No. 4,798,603 issued Jan. 17, 1989, to Meyer et al.; U.S. Pat. No. 4,710,187 issued Dec. 1, 1987, to Boland et al.; U.S. Pat. No. 4,770,656 issued Sep. 13, 1988, to Proxmire et al.; U.S. Pat. No. 4,762,521 issued Aug. 9, 1988, to Roessler et al.; U.S. Pat. No. 4,315,507 issued Feb. 16, 1982, to Whitehead; U.S. Pat. No. 3,881,490 issued May 6, 1975, to Whitehead; and U.S. Pat. No. 3,805,790 issued Apr. 23, 1974, to Kaczmarzyk, which patents are hereby incorporated by reference.

EXAMPLES

Test Methods
Odor Perception Test

Odor perception is, by its nature, a very subjective determination. According to the procedure, a small group of up to four samples are reviewed at one time. The samples to be tested are provided to a panel of two odor specialists who independently rank the urine-wet odor of the samples on a scale of 1 (least) to 10 (most) for malodor and intensity. Samples yielding an odor ranking below about 3.0 possess an odor which would hardly be noticed by the general public. The urine employed in the testing is a reconstituted urine (reconstituted according to product instructions), commercially available from Fischer Scientific under the trade designation UriChem® Urine Chemistry Control (Human) Level 1, Catalog No. 2934-80.

Surface-Active Agent Effectiveness Test

The following procedure is used to determine whether a specific surface-active agent is effective to reduce the odor of urine. A water-swellable, generally water-insoluble, hydrogel-forming polymeric absorbent material is prepared, as set forth in Example 1 which follows, with no surface-active agent being added to the polymerization mixture. The resulting polyacrylate is ground into particles and sieved as set forth in Example 1. The surface-active agent to be tested is dispersed in ethanol such that the surface-active agent is present in the ethanol in a concentration of 0.25 percent by weight. The solution of ethanol and surface-active agent is then sprayed on a portion of absorbent material to deposit a 0.1 weight percent coating.

1.5 grams of the coated, particulate water-swellable, generally water-insoluble absorbent material is placed in a watch glass. Four drops (about 0.2 milliliters) of reconstituted urine (UriChem®) is applied to the coated absorbent material. 1.5 grams of the particulate, water-swellable, generally water-insoluble, hydrogel-forming polymeric absorbent material having no surface-active agent coated thereon is placed in a watch glass and serves as a control sample. Four drops of reconstituted urine (UriChem®) is applied to the absorbent material (control). The two samples are then subjected to the Odor Perception Test described above. If the surface-active agent coated test sample receives a lower average ranking for malodor and intensity than the non-surface-active agent coated test sample (control), the surface-active agent being tested is considered effective to reduce the odor of urine.

Example 1

A variety of polyacrylate superabsorbent samples were prepared by a solution polymerization process. The samples were identical except for the concentration and identity of surface-active agent incorporated into the polymerization solution. The particular surface-active agents employed, and the concentrations at which they were employed, are set forth in Table 1. The solution polymerization was performed as follows. The polymerization was carried out at 70° C. in a stirred 1 liter resin flask equipped with a nitrogen sweep. To the resin flask was charged 173.3 grams of distilled water, 36 grams (0.5 mole) of acrylic acid, 15 grams (0.375 mole) of sodium hydroxide, 0.616 gram (0.004 mole) of N,N'-methylenebisacrylamide, 0.2 gram of sodium persulfate and 0–2 percent, by weight monomer, of a surface-active agent. The polymerization continued until essentially complete. The gel obtained from the reactor was cut into small pieces and dried in a convection oven at 100° C. overnight. The dry material was ground in a Waring blender to pass a U.S. standard 20 mesh sieve (850 micron openings) and be retained on a U.S. standard 100 mesh sieve (149 micron openings). Thus, the particles employed had a maximum cross sectional dimension within the range of from about 150 to about 850 micrometers.

1.5 grams of the water-swellable, generally water-insoluble, hydrogel-forming polymeric absorbent material prepared as described above was placed in a container such as a watch glass. To the container was added 4 drops of the reconstituted urine. A sample of each absorbent material was then subjected to the odor perception test described above. The results of the odor perception test are set forth below in Table 1. The samples are grouped by numbers such that samples with the same numerical grouping (e.g., 2A–2D) were subjected to odor testing at the same time. As discussed above, comparison between groupings of samples is not appropriate, as a control sample was not present in each of the groupings.

TABLE 1

| Sample No. | Surface-Active Agent | HLB | Odor Ranking |
|---|---|---|---|
| 1A* | None (control) | — | 7.9 |
| 1B* | 1% Triton-X-102 | 18 | 5.6 |
| 2A* | None (Control) | — | 7.1 |
| 2B* | 1% Tergitol 15-S-40 | 18 | 7.3 |
| 2C* | 1% Tergitol 15-S-15 | 15.6 | 6.7 |
| 2D | 2% Tergitol 15-S-5 | 10.6 | 3.2 |
| 3A | 1% Span 80 | 4.3 | 2.4 |
| 3B* | 1% Igepal CO-210 | 4.6 | 5.0 |
| 3C* | 1% Lexemul 530 | 5.o | 8.7 |
| 3D* | 1% Igepal CO-430 | 8.8 | 4.8 |
| 4A* | None (Control) | — | 4.5 |
| 4B | 1% Tween 81 | 10 | 2.8 |
| 4C* | 1% Unithox 450 | 10 | 4.0 |
| 4D | 1% Tergitol 15-S-5 | 10.6 | 2.4 |
| 5A* | None (Control) | — | 8.5 |
| 5B | 1% Tergitol 15-S-3 | 8.8 | 3.4 |
| 5C* | 1% Gemtex SM-33 | Unknown (>15) | 6.3 |

*Not an example of the present invention

As can be seen from reference to Table 1, surface-active agents having an HLB above about 12 do not generally produce a desirable odor ranking. Moreover, not all surface-active agents having an HLB below 12 are effective to reduce the odor of urine.

Example 2

A water-swellable, generally water-insoluble, hydrogel-forming polymeric absorbent material was prepared according to the process set forth in Example 1 except no surface-active agent was added to the polymerization mixture. The absorbent material thus prepared was coated with a variety of surface-active agents by dispersing the surface-active agent in ethanol such that the surface-active agent was present in the ethanol in a concentration of 0.25 percent by weight. The solution of ethanol and surface-active agent was then sprayed on the absorbent material to deposit a 0.1 percent by weight coating. Two control samples were prepared. The first control sample was the absorbent material as produced. The second control sample was treated with ethanol comprising no surface-active agent. Sample 6G was prepared by coating Perlite (a volcanic ash) particles with the indicated surface-active agent dispersed in ethanol. The solution of ethanol and surface-active agent was sprayed on the Perlite to deposit a 0.2 percent by weight coating. The coated Perlite was then blended with the non-coated first control sample of absorbent material in a ratio of 1 part treated Perlite to 4 parts absorbent material. The absorbent materials were then subjected to the Odor Perception rest as set forth above. The results of the testing are set forth in Table 2.

TABLE 2

| Sample No. | Surface-Active Agent | HLB | Odor Ranking |
| --- | --- | --- | --- |
| 6A* | None (control) | — | 8.2 |
| 6B* | None (control treated with ethanol) | — | 6.2 |
| 6C | Tween 81 | 10 | 2.5 |
| 6D | Span 80 | 4.3 | 2.5 |
| 6E | Tergitol 15-S-5 | 10.6 | 3.2 |
| 6F* | Gemtex SM-33 | Unknown (>15) | 6.1 |
| 6G | Tergitol 15-S-5 (coated on Perlite) | 10.6 | 3.3 |

*Not an example of the present invention

As can be seen from reference to Table 2, coating the absorbent material with an effective surfactant results in good odor reduction according to the present invention. This is true in spite of the fact that at least ten times less surface-active agent is used than when incorporated in the polymerization step (Example 1). Further, as can be seen from reference to sample 6G, coating the surface-active agent on Perlite and mixing the Perlite with the absorbent material is also effective to reduce the urine odor.

Example 3
(Prophetic)

Absorbent structures comprising wood pulp fluff and a water-swellable, generally water-insoluble, hydrogel-forming polymeric absorbent material are prepared by air laying a mixture of wood pulp fluff and absorbent material in a 90/10 weight ratio. The air-laid batts are cut to a sample size of 6×6 inches (15.2 cm×15.2 cm). The absorbent material employed is that prepared according to the polymerization recipe and method set forth in Example 1, except that no surface-active agent is added to the polymerization mixture. A surface-active agent is applied to the batts by forming a 10 weight percent solution of Tergitol 15-S-5 in ethyl alcohol. The solution of Tergitol 15-S-5 in ethyl alcohol is then sprayed on the batts in varying amounts. The batts are then dried and weighed to determine the loading of surface-active agent. Two inch by two inch test samples are then cut from the batts and insulted with approximately 6 drops of reconstituted urine (described above) and subjected to odor testing as described above. The results of this testing are set forth in Table 3.

TABLE 3

| Sample No. | Concentration of Surface-Active Agent | Odor Ranking |
| --- | --- | --- |
| 7A* | None (control) | 7.0 |
| 7B | 1.0% | 2.8 |
| 7C | 1.5% | 2.8 |
| 7D | 4.75% | 1.3 |

*Not an example of the present invention

As can be seen from reference to Table 3, application of the surface-active agent to a fluff batt containing a water-swellable, generally water-insoluble, hydrogel-forming polymeric absorbent material is an effective way to reduce the odor of urine applied to the fluff batt. This example is prophetic. The results reported were obtained by conducting this example as described, except no absorbent material was present in the air laid batts. The inclusion of the absorbent material is not believed to affect the relative odor ranking; nonetheless, the actual numbers may vary.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. A method for reducing malodor associated with a disposable absorbent product intended for the absorption of body fluid, said method comprising the step of:

applying to said absorbent product comprising an absorbent structure exhibiting a weight and comprising from about 30 to 100 weight percent, based on total weight of the absorbent structure, of a hydrogel-forming polymeric material, prior to use of the absorbent product, a surface-active agent selected from the group consisting of ethoxylated sorbitan mono-oleate, mono-oleate, and ethoxylated $C_{11}$–$C_{15}$ secondary alcohols, having a hydrophilic/-lipophilic balance (HLB) of less than about 12 wherein said surface-active agent is applied to the absorbent product in an amount of from about 0.005 to about 25 weight percent based on total weight of the hydrogel-forming polymeric material.

2. The method according to claim 1 wherein the amount of surface-active agent applied to said absorbent product is from about 0.1 to about 10 weight percent, based on the weight of the hydrogel-forming polymeric material.

3. The method according to claim 2 wherein the amount of surface-active agent applied to said absorbent product is from about 0.5 to about 5 weight percent, based on the weight of said hydrogel-forming polymeric absorbent material.

4. The method according to claim 1 wherein the surface-active agent has a hydrophilic/lipophilic balance of less than about 11.

5. The method according to claim 1 wherein the surface-active agent is present in said absorbent structure in an amount of less than about 10 percent by weight, based on the weight of the hydrogel-forming polymeric material present in said absorbent structure.

6. The method according to claim 5 wherein the surface-active agent is present in said absorbent structure in an amount of less than about 5 percent by weight, based on total weight of said hydrogel-forming polymeric absorbent material present in said absorbent structure.

7. The method according to claim 1 wherein said surface-active agent is sprayed on said absorbent product.

8. The method according to claim 1 wherein said surface-active agent is incorporated into said hydrogel-forming polymeric absorbent material during polymerization of the absorbent material.

9. The method according to claim 1 wherein said surface-active agent is coated on said hydrogel-forming polymeric absorbent material.

10. The method according to claim 1 wherein at least about 2 percent of said hydrogel-forming polymeric absorbent material has a particle size of less than about 200 micrometers.

11. The method according to claim 10 wherein said hydrogel-forming polymeric absorbent material is solution polymerized.

* * * * *

UNITED STATES PATENT AND TRADEMARK OFFICE
CERTIFICATE OF CORRECTION

PATENT NO. : 5,961,504
APPLICATION NO. : 08/164112
DATED : October 5, 1999
INVENTOR(S) : James Richard Gross It is certified that error appears in the above-identified patent and that said Letters Patent is hereby corrected as shown below:

| | |
|---|---|
| Column 1, Line 26: | Change "U.S. Pat. No." to --U.S. Patent--. |
| Column 5, Line 7: | Change "affect the product product in" to --affect the product in--. |
| Column 7, Line 17: | Change "U.S. Pat. No." to --U.S. Patent--. |
| Column 7, Line 18: | Change "Jan." to --January--. |
| Column 7, Line 18: | Change "U.S. Pat. No." to --U.S. Patent--. |
| Column 7, Line 19: | Change "Dec." to --December--. |
| Column 7, Line 19: | Change "U.S. Pat. No." to --U.S. Patent--. |
| Column 7, Line 20: | Change "Sep." to --September--. |
| Column 7, Line 21 & 22: | Change "U.S. Pat. No." to --U.S. Patent--. |
| Column 7, Line 22: | Change "Aug." to --August--. |
| Column 7, Line 23: | Change "U.S. Pat. No." to --U.S. Patent--. |
| Column 7, Line 23: | Change "Feb." to --February--. |
| Column 7, Line 24: | Change "U.S. Pat. No." to --U.S. Patent--. |

UNITED STATES PATENT AND TRADEMARK OFFICE
CERTIFICATE OF CORRECTION

PATENT NO. : 5,961,504
APPLICATION NO. : 08/164112
DATED : October 5, 1999
INVENTOR(S) : James Richard Gross It is certified that error appears in the above-identified patent and that said Letters Patent is hereby corrected as shown below:

Column 7, Line 25:  Change "U.S. Pat. No." to --U.S. Patent--.

Column 7, Line 25:  Change "Apr." to --April--.

Column 10, Line 46:  Change "hydrophilic/-lipophilic" to --hydrophilic/lipophilic--.

Signed and Sealed this

Fifth Day of February, 2008

JON W. DUDAS
*Director of the United States Patent and Trademark Office*